(12) United States Patent
Wolf et al.

(10) Patent No.: US 9,702,809 B2
(45) Date of Patent: Jul. 11, 2017

(54) TRIBOMETER, RHEOMETER, MODULE AND A METHOD FOR TRIBOLOGICAL MEASUREMENTS

(71) Applicant: ANTON PAAR GMBH, Graz-Strassgang (AT)

(72) Inventors: Frederik Wolf, Stuttgart (DE); Bernhard Bauer, Lebring (AT); Michael Krenn, Zettling (AT)

(73) Assignee: Anton Paar GmbH, Graz-Strassgang (AT)

( * ) Notice: Subject to any disclaimer, the term of this patent is extended or adjusted under 35 U.S.C. 154(b) by 109 days.

(21) Appl. No.: 14/479,525

(22) Filed: Sep. 8, 2014

(65) Prior Publication Data
US 2015/0068273 A1     Mar. 12, 2015

(30) Foreign Application Priority Data

Sep. 6, 2013   (AT) .............................. A 50562/2013

(51) Int. Cl.
*G01N 19/02*      (2006.01)
*G01N 11/00*      (2006.01)
(Continued)

(52) U.S. Cl.
CPC ............. *G01N 19/02* (2013.01); *G01N 11/00* (2013.01); *G01N 11/14* (2013.01); *G01N 33/30* (2013.01)

(58) Field of Classification Search
CPC ........ G01N 19/02; G01N 19/00; G01N 11/00; G01N 11/14; G01N 33/00; G01N 33/02; G01N 33/30
See application file for complete search history.

(56) References Cited

U.S. PATENT DOCUMENTS

| | | | | |
|---|---|---|---|---|
| 5,377,525 A | * | 1/1995 | Hutchinson | ............ G01N 33/30 73/10 |
| 5,861,954 A | * | 1/1999 | Israelachvili | .......... G01N 19/02 356/496 |

(Continued)

FOREIGN PATENT DOCUMENTS

| | | |
|---|---|---|
| AT | 505938 B1 | 5/2009 |
| AT | 508706 B1 | 6/2011 |

(Continued)

*Primary Examiner* — Nguyen Ha
*Assistant Examiner* — Wyn' Ha
(74) *Attorney, Agent, or Firm* — Laurence A. Greenberg; Werner H. Stemer; Ralph E. Locher (57) ABSTRACT

A method and a device measure tribological values of samples with a rheometer. Wherein measuring parts of the rheometer are replaced by the samples and the surfaces of the samples are moved into frictional contact relative to each other. Accordingly, it is provided that all parts of the rheometer supporting the samples in frictional connection or frictional contact and forming the rheometer power circuit, including a spring unit pressing the samples against each other, are regarded as an oscillatory circuit. Oscillation properties of the spring unit are relevant to oscillation properties of the oscillatory circuit. The oscillation properties of the spring unit are adjusted taking into consideration resonance oscillations or effects produced by changing or different measurement conditions expected with the respective measurement.

6 Claims, 9 Drawing Sheets

(51) Int. Cl.
   *G01N 11/14*    (2006.01)
   *G01N 33/30*    (2006.01)

(56) References Cited

U.S. PATENT DOCUMENTS

| | | |
|---|---|---|
| 8,413,481 B2 | 4/2013 | Debon et al. |
| 8,453,496 B2 | 6/2013 | Läuger et al. |
| 2014/0290378 A1* | 10/2014 | Hou ........................ G01N 19/00 73/818 |

FOREIGN PATENT DOCUMENTS

| | | | |
|---|---|---|---|
| EP | 2150800 A1 | 2/2010 | |
| JP | 2009236924 A * | 10/2009 | ............. G01N 11/16 |
| WO | 2008148536 A1 | 12/2008 | |

* cited by examiner

TRIBOMETER, RHEOMETER, MODULE AND A METHOD FOR TRIBOLOGICAL MEASUREMENTS

CROSS-REFERENCE TO RELATED APPLICATION

This application claims the priority, under 35 U.S.C. §119, of Austrian application AT A 50562/2013, filed Sep. 6, 2013; the prior application is herewith incorporated by reference in its entirety.

BACKGROUND OF THE INVENTION

Field of the Invention

The invention relates to determining tribological parameters and measured values. Furthermore, the invention relates to a module, that is, a tribology cell, for use in such a process. Finally, the invention relates to a rheometer for implementing a method, if need be, using a module according to the present invention.

Rheology by definition deals with the deformation and the flow behavior of substances. Rotational rheometers are measurement devices for examining the rheological properties of different material samples. In the process, a measuring sample to be examined is introduced into a generally narrow measuring gap between two measuring parts of the rotational rheometer, the two measuring parts are then rotated and/or oscillated relative to each other and the material sample is subjected to a shear stress between the measuring parts. Elastic functions for example of the material sample are obtained from the axial/normal forces, e.g., of a cone-plate-rheometer or a plate-plate-rheometer, acting perpendicular to a shear plane. Rotational rheometers make possible the combination of a multiplicity of different experiments, in which either shear stress, shear deformation, or shear speed can be predetermined. Rotational rheometers can in principle possess different designs with a measurement motor, a rotational motor and separate measurement motor or a combination of two measurement motors and are described for example in Austrian patent AT 508706 B1 of the applicant.

The torque determination of the rotational rheometer can be made with two motor units separated from each other for drive/rotation and torque determination, which are assigned to one of the measuring parts. Furthermore, double motor systems with two measurement motors are also known, see, for example, Austrian patent AT 508 706 B1. In addition, different systems for determining the normal forces (axial forces) occurring are known.

On the other hand, tribology deals in general with relative movement of surfaces of samples under the application of a normal force on each other. Friction, wear, and lubrication are examined with the goal of characterizing and if necessary optimizing moving parts in movement systems. The measurement of the friction coefficients is made here particularly over longer time periods on tribological pairings made of different materials with and without lubrication, wherein the parameters of normal force or pressure, sliding speed, and temperature can be varied during the measurement. Tribometers are devices for measuring tribological parameters. Tribometers can resemble rheometers except for design of the measuring parts/holder of the samples to be measured.

For tribological measurements the frictional contact between the areas to be examined is decisive. The contact is measured in practice, lubricated or unlubricated, that is, with or without an intermediate layer of a material, between two samples made of material to be measured or the different materials to be measured.

Due to the extremely wide range of issues in tribology numerous tribometers had been developed for certain cases of application and measurement tasks. The interpretation and transferability of results obtained on tribometers is challenging. Since the tribological characteristic values are always system characteristic values, the specification of individual values such as friction values is for the most part not constructive without specifying the exact test conditions. For example, the results are used for the characterization of lubricants or the design of bearings and for applications in many subject areas from the cosmetics industry, food industry, to drive and control technology up to mechanical engineering.

Due to the same order of magnitude of the measured values occurring, the possibility of specifying the normal forces as well as the precise specification and measurement of speed and torque, rheometers are suitable in terms of design in principle for use in high-precision tribological systems, particularly when the measuring/holding parts of the rheometer are arranged interchangeably and can be replaced by a holder for samples to be measured/examined for tribological parameters. The samples to be examined may be already configured to be in a form of measuring parts or applied to measuring parts of rheometers, or special sample holders may be connected with the measuring shafts of the rheometer or configured as such and brought into direct contact with each other. Such an arrangement is described for the special case of the characterization of ball bearings in Austrian patent AT 505938. An application for the characterization of the friction properties of food with special interfaces is described in published, European patent application EP 2150800 A1.

For the conversion of a rheometer into a tribometer it is thus merely required to replace the measuring/holding parts limiting the measuring gap of the rheometer with samples to be measured, or a module receiving the samples the module brings the samples into frictional contact. The equipment already available with rheometers is used for exerting an axial force or for measurement of the applied axial force in order to adjust the pressure of the areas of the samples opposite each other. In order to center the samples abutting each other with frictional contact or to hold them in abutment, springs or spring units or torsionally stiff couplings such as cardan joints are provided, which connect directly to the samples, if need be, via a sample holder, and if necessary the sample holder may be connected via a carrier to drive shafts or bearings of the rheometer having the measuring/holding parts already removed.

In performing rheological tests the height of the gap between the measuring parts of the rheometer, between which the sample to be measured is introduced, should be kept constant with high precision. For this to succeed, the rheometers are configured axially very stiff. Remaining low compliance is characterized by the so-called compliance of the system. Thus, a rheometer in practice may have a spring constant with great stiffnesss in its path or circle of force. Also, in the tribological test the surfaces of all samples in frictional contact should be pressed together with as equal and temporally constant force effect as possible. At the same time, the magnitude of the force should be able to be freely adjusted corresponding to the material pairings to be examined and the size of the contact area. The surface pressure is produced via the normal force regulation of the rheometer.

The rheometer or the rheometer stiffness or compliance can be depicted in this dynamic oscillation system as a spring with a high degree of stiffness. However, flatness imperfections in the sample surface and deviations from the ideal geometry produce normal forces, which change the application of force and thus falsify the measurement. In conventional tribology measuring devices this is not normally taken into consideration but nevertheless has been considered and solved to a degree. In particular, this also applies where stick-slip effects occur.

At the same time, the rotating parts of the measuring system should be aligned radially in all tribological turning experiments with the rheometer being as accurately as possible, in order to prevent the occurrence of shear forces, which falsify the measurement results. Especially in the case of several contact areas it is necessary to center the arrangement of all measuring parts precisely, in order to guarantee a uniform loading of the tribological contacts. Moreover, rotational rheometers have measuring shafts mounted as frictionless as possible in their design, which frequently have only low tolerance to shear forces, since the bearing can receive only low shear forces.

In the prior art these problems are solved to a degree, for example, by the use of cardan joints or springs in the axis of the measuring part. These elements make possible a radial displacement between the measuring system and air bearing, so that the measuring body of the possibly changing surfaces and/or force effects can follow. However, especially in the case of higher speeds, these systems offer less stability and can, where applicable, run or strike irregularly.

However, with springs and flexible torsionally stiff couplings an element with an additional spring effect or a further compliance is introduced into the force flow or the power circuit of the measurement system. This additional compliance is characterized by a spring constant other than the rheometer compliance.

However, this additional spring in the system brings with it the problem that certain natural frequencies of the system can lead to resonances, which can lead to the upswing of the rheometer or the system in the case of certain forces, oscillations, or angular speeds and changing surface shape, particularly due to irregular particles of an intermediate layer—thus a part of the measurement range, which in principle can be over-swept, can bring falsified results and cannot be used.

In commercial rheometers at most forces of 1 mN to 70 N and speeds of 0 to 3000 rpm are preset and/or measured. In principle, these ranges may also be preset and/or measured for tribological measurements, particularly when using and installing suitable motors and bearings these ranges can also be expanded. For tribological measurements total contact pressing forces of 0.1 N to 70 N are generally used, the rotation tests for the tribological characterization can be carried out with the angular speeds and angular acceleration available.

The spring additionally provided can through dynamic effects limit the measurement range available in principle by the occurrence of resonances. Which combinations of speed and force are affected thereby depends strongly on the actual sample combination. A reliable forecast of these measurement ranges, which are unusable or to be masked out, is very difficult or frequently not possible to obtain in prior art. This applies in particular in the examination of stick-slip effects on samples.

Figure 1:
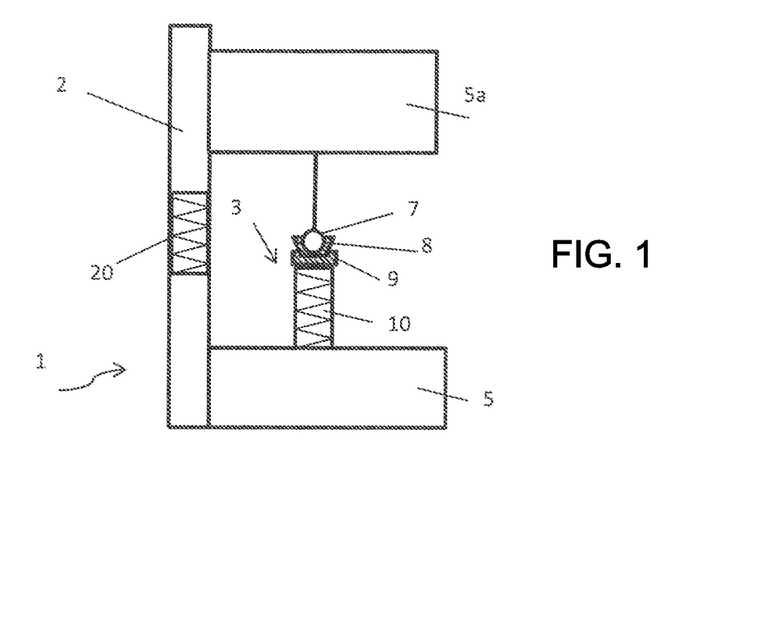
FIG. 1 is an illustration of a basic rheometer used for tribological measurements.

A rheometer, when used for tribological measurements, can be considered in principle to be a system with two springs 10, 20, just as this is depicted in FIG. 1. The spring 20 characterizes the spring properties of the device or the frictional connection, without considering the additionally installed spring 10 of the spring unit 3. The rheometer can here as in the prior art usually have one or two motors for the rotation and/or torque measurement and/or axial normal force specification, which are connected via a stand 2 adjustable for height. The motors are thereby firmly connected or interchangeably fixed to the base 5 and/or the overhanging arm 5a and are not considered separately in this illustration, the bearings of the measurement shafts contribute to the overall compliance of the rheometer.

By reference to Austrian patents AT 508706 B1 and AT 505938 B1 and published, European patent application EP 2150800 A1 mentioned at the outset the structure is or the features of the rheometer described there are assumed in this application to be a basic and possible structure of a rheometer according to the present invention and should be regarded as disclosed in the present application.

However, the additional relatively soft spring 10 in the spring unit 3 besides the spring 20 in the system brings with it the problem that certain resonance frequencies in the speed range of the system can lead to an upswing. This also applies to possible additional spring effects in connection with a cardan joint used, since also here certain compliance occurs, which is less than the compliance of the system.

If the system or the oscillatory circuit preset or produced by the frictional connection are considered more closely, the effect of resonance frequencies produced by the spring unit 3 must be taken into consideration as well as any problem arising due to changing, characterizing, etc., so as to reduce or cancel resonance effects of the system or the oscillatory circuit. Here the invention applies.

The compliance or overall compliance of a rheometer must be evaluated in principle in the frictional connection system. This overall-compliance can be characterized by the overall spring constant of the system $C_{overall}$. Due to the large spring constant (C1) of the spring 20 (of the oscillatory circuit), the lame spring constant (C1) is neglected or no longer considered in the determination of the overall spring stiffness $C_{overall}$ based on the comparatively large compliance and thus small spring constant (C2) of the spring 10 of the spring unit 3 according to the relationship $1/C_{overall}=1/C1+1/C2$. The overall stiffness of the rheometer thus corresponds approximately to the stiffness of the softer spring 10 used, approximately characterized by the spring constant C2. If one considers the system more precisely, the damping effect of the spring unit 3 must be taken into consideration.

Figure 2:
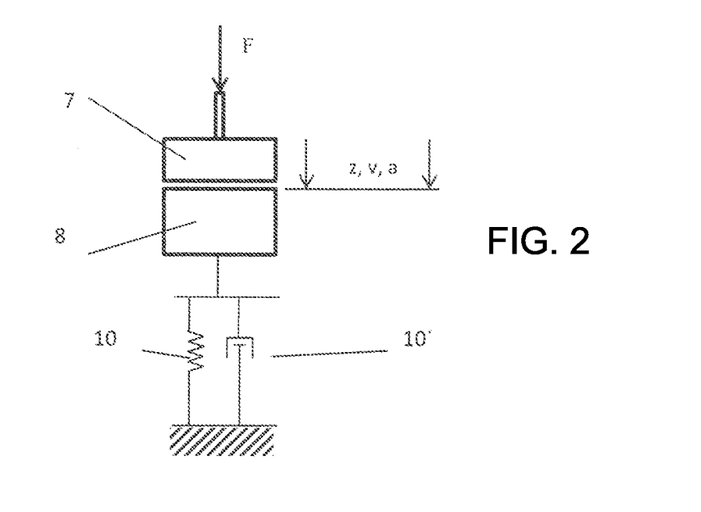
FIG. 2 is a simplified equivalent circuit diagram for a tribological contact.

FIG. 2 shows a simplified equivalent circuit diagram for the tribological contact between an upper and lower sample 7, 8 with spring effect 10 and damping effect 10' in the z-direction below the lower sample 8. Both of the samples 7, 8 are pressed together with the force F. If the distance between the samples 7, 8 changes as a result of component defects, resonances, stick-slip effects, oscillatory effects, etc. or even variation of one of the surfaces through flatness imperfection, then a dynamic force results. For this additional dynamic or temporally variable force F(t) the following motion equation applies in the z-direction with distance z, velocity v=dz/dt and acceleration $a=d^2z/dt^2$:

$$F(t)=m \cdot a + d \cdot v + c \cdot z,$$

wherein d is the viscous damping, c the spring constant, and m the total mass of the parts movable or moved during a distance change of the samples 7, 8. These parts are above all the samples 7, 8, as well as the spring 10 and possibly the holder for the samples 7, 8.

If in the process the force effect should remain as constant as possible, then the temporary dynamic force F(t) must remain as small or low as possible relative to F. This is the case if a) the moved part of the spring unit has overall as little mass as possible, in order to keep component m·a low, and
a, v and z remain as small as possible.

The moving masses should therefore be such that they can follow the movements of the samples in the x-y- and z-direction under as little force as possible.

Thus, the spring element 3 should have little mass and should preferably be arranged near the tribological contact, in order to avoid connection parts or to keep them as low in mass as possible.

Advantageously the spring element 3 should operate only in the z-direction.

For the natural frequency of the system $\omega^2 = c/m$ applies. The amplification function of such a system or oscillatory circuit can be influenced in respect to amplitude via the damping, at the same time the resonance frequency changes to a certain extent, a change in the resonance frequency can occur through adjustment of the spring constant or spring stiffness and/or the mass in the oscillatory circuit.

SUMMARY OF THE INVENTION

Thus, according to the present invention it is proposed to control, to minimize or to eliminate the problem of resonance effects in a process of the type mentioned at the outset, that all parts of the rheometer holding the samples in frictional connection and frictional contact or forming path or circle of force of the rheometer, including the spring unit, are regarded as an oscillatory circuit. The oscillation properties of the spring unit are regarded as relevant and sufficiently representative for the oscillation properties of the oscillatory circuit, and that before the start and/or during measuring the values the oscillation properties of the spring unit are set or adjusted or turned off taking into consideration the resonance oscillations or effects produced by changing, different measurement conditions, in particular samples possessing different masses, changes of the frictional resistance and/or changes of the axial forces occurring, which are expected with the respective measurement. The measured values obtained are evaluated.

For the definition of the oscillatory circuit formed in the rheometer, the compliance or stiffness of which is set in relation to the stiffness or compliance of the spring element, it is advisable, if all parts of the rheometer participating in the path or circle of force of the rheometer for the application of force to the surfaces of the samples in frictional contact or located in the path or circle of force, in particular equipment base, stand, support arm, drive and measurement shafts, sample holder and bearing, are included in the oscillatory circuit.

This ensures that the component parts that play a role in the forces acting at the frictional contact are taken into consideration by way of their effective forces in the oscillatory circuit. The path or circle of force includes all of the forces acting in the closed system.

For an estimation of the magnitude to be taken into consideration or of the oscillation properties it is advantageous, if, the spring-elastic movable sections of the at least one spring of the respective spring unit, the mass of a holder born by the respective spring and/or of a holding area located on the spring for the samples, the mass of the spring-elastic unmovable parts of the spring unit between the mounting location or the stationary, unmovable base point of the spring and the tribological contact point of the sample supported by the spring and if necessary the mass of the samples are regarded as relevant for the oscillation properties of the spring unit or are consulted for a possible modification.

It has proven to be advantageous for practice, if for the setting of the oscillation properties of the spring unit the stiffness of the spring or the spring constant of the spring is changed, preferably by changing the spring length or the spring-effective portion of the total spring length of the spring, and/or the mass of the samples and/or the mass of the spring-elastic unmovable parts of the spring unit is changed, particularly by adding or removing masses attachable to or removable from the samples or the spring-elastic unmovable parts of the spring unit, preferably the holder or holding area, and/or if the oscillation movement of the spring is braked or damped by an attenuator engaging the respective sample and/or the spring-elastic unmovable parts.

It is now also possible, that between the surfaces of the samples in frictional contact an intermediate layer or interlayer made of material influencing the friction between the surfaces is introduced, without undesired resonance oscillations occurring. Oscillatory processes caused by different introduced materials can be successfully influenced and examined.

A simple implementation of measurements results, if the force, with which the samples are pressed against each other is adjusted with a control circuit.

The measurement and the measurement preparations are simplified, if the spring constant or compliance of the parts of the rheometer forming the oscillatory circuit remain unchanged during the setting or adjustment of the oscillation properties of the spring unit.

A module according to the present invention of the type mentioned at the outset is characterized in that the spring and the holder or holding area are regarded as parts of a mechanical oscillation system and determine its oscillation properties, and that an adjustment unit is provided, with which the oscillation properties of the oscillation system are adjustable or alterable. Such a module is advantageously suitable to implement the method according to the present invention or to be used in a rheometer, in order to be able to take tribological measurements with a conventional rheometer and to thereby influence resonance oscillations in the measurement operation.

In the case of such a module it is provided according to the present invention, that with the adjustment unit the spring constant of the spring is alterable and the adjustment unit, if necessary, has at least one component applicable against or applying a load to the spring, which adjusts the spring effective length of the spring, and/or that with the adjustment unit the mass borne by the spring is alterable and the adjustment unit, if necessary, has a container located on the spring and/or on the holder for the defined input or removal of a medium, preferably of a liquid, and/or that the adjustment unit contains an element mechanically damping the movement of the spring and/or of the holder and/or of the sample through frictional resistance, if necessary, in the form of friction parts supported on the spring. Thus, an adjustment or alteration of the oscillation properties of the module can be achieved easily, whereby the measuring range is enlarged or resonance frequencies prevented.

In the case of special embodiments of the module it is provided that a holder carrier bears at least one plate, from which at least one spring, preferably a multiplicity of springs, departs in each case in the form of a flat spring aligned parallel to the plate, which in its free end area, if necessary via a holder, bears a sample. For each flat spring, a clamping component is provided, with which the body of the spring is loadable and securable in respect to its plate distance from different, especially continuously changeable installation positions. If necessary the clamping component has the form of spokes rotatable about the holder, which can be applied against the flat springs aligned essentially in the circumferential direction of the plate and if necessary can be fixed in different installation positions. In the case of another embodiment it can be provided that the spring is configured in the form of a flat spring arranged in particular horizontally, which is supported on supports lying on both sides of its longitudinal middle area, that the holder for the samples is supported in the longitudinal middle area of the flat spring, if necessary, via a slide stone guided movably in the x-y direction, and that the supports are adjustable along the flat spring, particularly at the same time and with the same feed, wherefore, if necessary, the supports are guided into spiral grooves of a base plate arranged beneath the flat spring and are arranged movably towards each other or away from each other during the twisting of the spiral grooves in the longitudinal direction of the flat spring.

A simple structure results if the sample is held with a holder on the spring in a holding area of the spring or is directly fastened to the spring, e.g., is screwed in, clamped, or welded on.

A rheometer according to the present invention contains a first carrier near the rheometer and a second carrier also near the rheometer, which in each case support a sample. The carriers are received by the measuring part accommodations or connections or measurement or drive shaft connections of the rheometer or are formed by removable or insertable measurement shafts. At least one of the two carriers in each case supports at least one spring, which supports at least one sample via a holder or holding area. Drive units for the rotation of at least one carrier with preset speed and/or preset torque are provided. Measurement units are provided for measuring the speed and torque which is applied or occurs. A compressive force unit presses the samples into mutual frictional contact, which if necessary has a control unit for compressive forces to be applied. At least one of the carriers as well as the at least one spring supported by the latter and the holder or holding area located on the spring are designed in the form of a module.

More generally, the following is now explained regarding the method or the module or rotational rheometer according to the present invention.

One or more samples each can be borne by a spring unit. The spring units possess springs, which in each case load one of the samples or springs, which jointly load all of the samples. It is also possible to assign a spring unit in each case to the samples lying on both sides of the tribological contact area. Thus, the possibility of undesired resonances is indeed doubled; however, in the present invention, these resonances are controllable or alterable by an appropriate change of the spring characteristics of one or both spring units. For this purpose, the spring units lying on both sides of the tribological contact areas can be altered with respect to their oscillation behavior so as to control resonances.

The spring units can have different types of springs, e.g. flat springs, spiral springs, helical compression springs or the like.

The spring units can be arranged in a rotationally invariant manner or can be rotated with the respective samples at the preset speed.

The arrangement and the structure of the springs or of the carrier supporting the springs is such that during the rotation of the samples no radial oscillations occur. Advantageously, the spring units possess a symmetrical structure or comprise congruently structured sections.

The invention makes it possible if necessary also to automatically implement an adjustment or a setting of the spring constant of the spring and/or of the mass of the spring element depending on the measurement problem in order to control resonances.

In principle, the springs of the spring units can also be exchanged and be replaced by thinnner, softer, or by thicker, harder springs. In addition or alternatively, the oscillating masses of the spring units can be changed, whereby the oscillation behavior of the spring units changes.

It is easily possible for a person skilled in the art to make the required setting of the oscillation properties of the spring units. It is sufficient for practice, to make a small number usually not more than two test sample measurements, preferably with the application of force of the test samples used preset for the measurement and the preset measurement parameters or the preset speeds or torques. Here the measurement ranges are readily recognized, in which resonance oscillations occur. These resonance oscillations are then eliminated from the measurement range by modification of the spring constants or the mass of the spring unit or setting attenuators before an actual measurement process is started. Alternatively, the resonance oscillations can also be specifically examined.

The possibility also exists to select and use differently designed modules, i.e., modules, which differ in respect to the spring characteristics and/or masses and/or damping and are thus adapted to different samples.

If a test sample and a sample to be examined have the same mass, it is easily possible to make calibration measurements in advance and to select appropriate spring units or modules depending on a calibration table, in order to find trouble-free measurement areas for different measurement conditions.

The samples can be inserted into holders, which are connected with the spring or are formed directly on the latter. It is also possible to mount the samples directly on the spring, e.g. to clamp, weld, screw, or stick, etc. them on. In these areas the spring cannot oscillate and these holding areas must thus be assigned to the mass of the spring element, the holding areas constitute sections of the spring, which are not spring-elastic. Additional masses can also advantageously be mounted in these holding areas of the spring and on holders easily and with little trouble. The additional masses can also be mounted on the samples.

The change of the spring characteristic of the spring can be advantageously made by changing its parts or sections which are able to oscillate. Advantageously, the section of the spring near to or distant from the carrier can be secured over a more or less large length with a retaining part and can be prevented from oscillating.

Moreover, the possibility exists of changing the spring stiffness of the spring element by exchanging or adding springs or spring packets.

In principle, it is possible to design the spring element, which holds the samples in frictional contact, electromagnetically, magnetically, pneumatically, or hydraulically. All such systems have their own oscillation characteristics or can cause resonance oscillations, which change the measurement conditions. In the present invention, such systems can also be set with regard to their oscillation properties before the measurement starts and such systems are to be regarded as equivalent to a mechanical spring unit.

The spring effect of a pneumatic system can, for example, be influenced or changed by volume and/or pressure changes in the piston or pressure chambers loading the samples and/or by mass changes of the masses moved. A change of the oscillation properties of a magnetic coil can occur, for example, as a result of changes in the supply voltage and/or supply current and/or mass changes.

It is also possible, for example, to adjust the spring constant of a spiral spring by an adjustment mechanisms, while the effective spring length of the spiral spring, if necessary, is changed by continuous changes in the length of the spring-elastic body.

The location of the support points of a spring, for example, a flat spring, can also be changed via the spring length, since by changing the location of the installation points of the support of the spring the spring properties of the spring are accordingly changed.

It can be advantageous, if the spring stiffness can be automatically adjusted by an adjustment mechanism, so that before carrying out a measurement, a desired change or setting can be made in a simple manner, if necessary, to be controlled by a provided evaluation and control unit.

A possibility for setting the spring characteristic exists in the adjustment of the oscillation properties by changing the mass, which more generally can be done by installing or removing mass elements if need be of different sizes in or from the spring unit. For example, fluids can be poured into containers or removed from them. The containers and/or masses used, in particular liquids, can occupy a preset volume which varies from case to case and/or have different density.

A rheometer used for tribological measurements has accommodations for modules or tribocells according to the present invention, to which the carrier of the samples and/or the spring units are adapted.

Other features which are considered as characteristic for the invention are set forth in the appended claims.

Although the invention is illustrated and described herein as embodied in a tribometer and a method for tribological measurements, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 3:
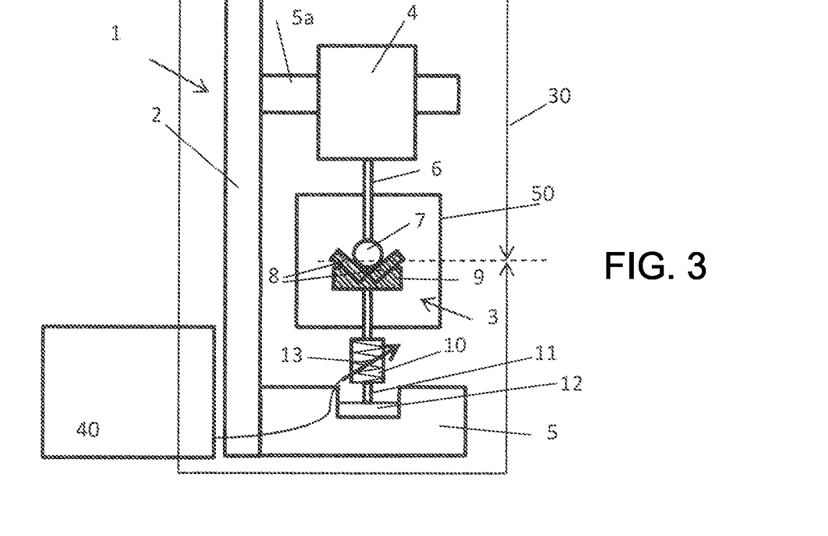
FIG. 3 is an illustration showing a basic structure of a rheometer according to the invention.

Referring now to the figures of the drawings in detail and first, particularly to FIG. 3 thereof, there is shown a rheometer 1 that contains a measurement motor 4 and a measurement shaft 6 connected to the latter, on a lower end of which a sample 7 is mounted in the form of a ball. With a normal force control unit arranged for example in an evaluation and control unit 40 the sample 7 can be pressed with defined force against a sample 8 located below, particularly through prior lowering of an overhanging arm 5a. Three lower samples 8 mounted symmetrically to each other in the form of leaves are in tribological contact with the ball 7. The leaves 8 are supported by a holder 9, which is supported subsequently by a spring 10. The holder 9 and the spring 10 define the spring unit designated as 3, which extends over a length of arrow 3'. The spring constant of the spring unit 3 can advantageously, if need be automatically, be changed via the control and evaluation unit 40 by an adjustment mechanism or adjustment unit 13. The spring unit 3 is located on a carrier 11, which is insertable and if necessary drivable into a bearing 12 of the rheometer 1 which is near the base. In the present case the sample 7 is rotated with the measurement shaft 6.

The spring properties of the spring unit 3 are representative of the spring properties of the entire rheometer 1 or of an oscillatory circuit 30, which, as indicated by the arrow, comprise all of the movable, particularly spring-elastic movable parts of the rheometer 1 in the path or circle of force, or power circuit, which are deformable when force is applied to the samples 7, 8 and thus have the possibility of appearing spring-effectively or of exerting forces on the samples 7, 8, which can generate resonances or oscillations in the oscillatory circuit 30.

Together with the carrier 11 the spring unit 3 constitutes a module or a tribological measurement module/cell insertable into a rheometer 1 according to the present invention. The spring unit 3 with the carrier 11 can be exchangeably integrated into the rheometer 1 or constitutes an installable and removable component assembly, and at least one of the measurement parts of the rheometer 1 can be exchanged for this component assembly or for the module according to the present invention. Another measurement part of the rheometer 1 is replaced by a sample or also a module. Thus, the spring unit 3 can also be provided for the upper sample 7 depicted in FIG. 3, so that the samples 7, 8 are loaded overall by two spring units 3, in which the spring characteristic can be changed or adjusted.

If the measurements are performed in the extreme temperature range, then it is advantageous to provide the spring 10 outside the range tempered for the tribological contact, in order to prevent temperature influences. Samples 7, 8 can be arranged within a tempering chamber 50, which surrounds the tribological contact. The tempering parts can also be integrated into the holders 9 for the samples 7, 8. Particularly, resistance heaters and peltier elements are worth considering for this.

The spring 10 can be arranged in the spring unit 3 such that it can be exchanged, for example, by a clamping tool with a quick-release connector and an adjustment of the spring unit 3 can be made by use or exchange of springs having a different spring characteristic. Thus, a number of modules can be made available, which can be exchanged to adjust the spring characteristic of the respective rheometer to each measurement situation given.

Figure 4:
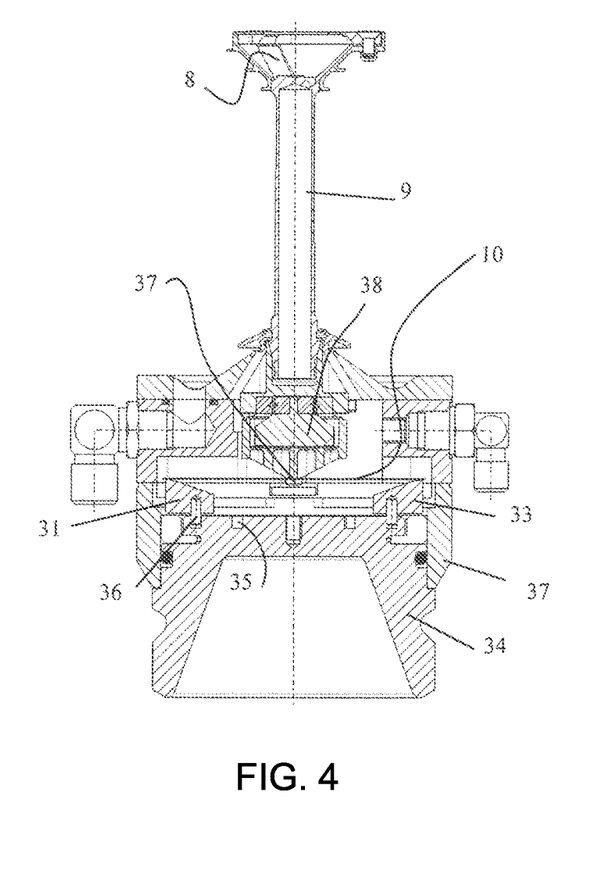
FIGS. 4 and 4A are diagrammatic, sectional views of an embodiment of a module.
Figure 4A:
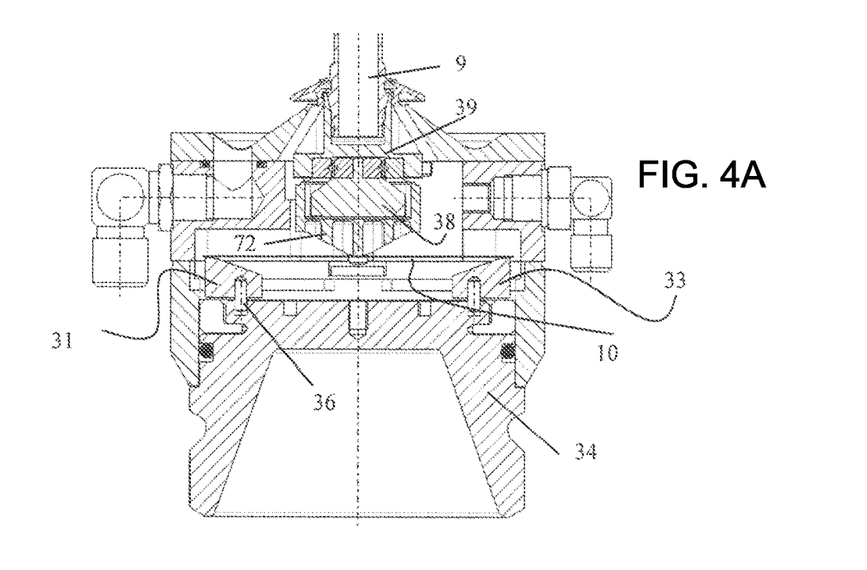
Figure 5:
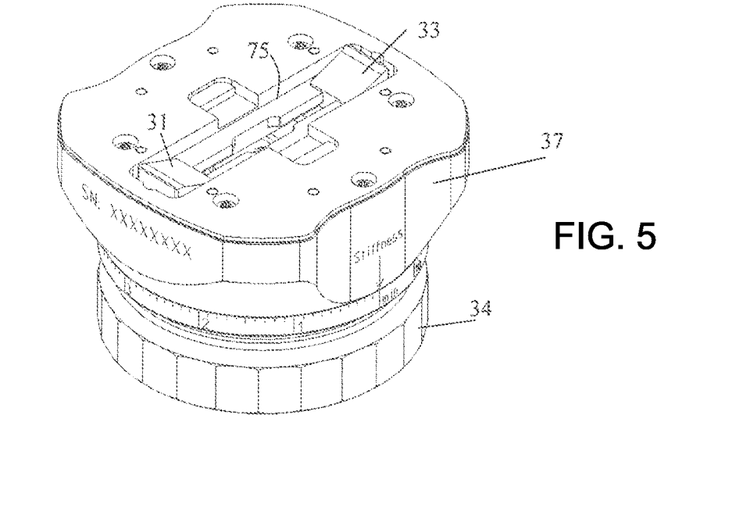
FIGS. 5 and 5A are perspective views showing details from FIG. 4.
Figure 5A:
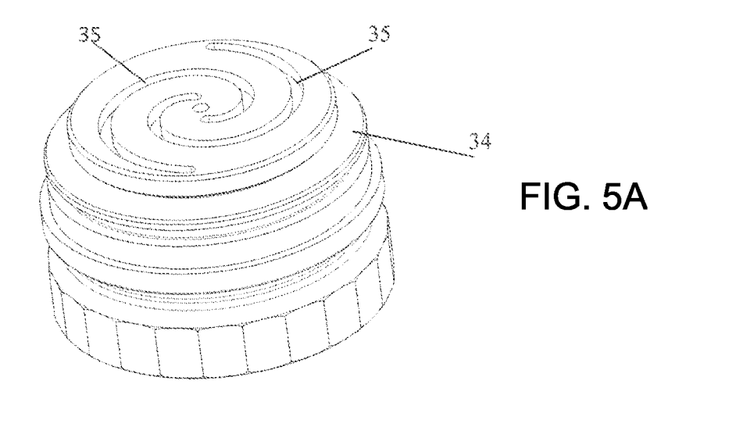

In FIGS. 4 and 4A an embodiment of a module according to the present invention is represented, which is insertable into a rheometer. The spring unit 3 contains a flat spring 10, which is essentially aligned in a horizontal plane and in its longitudinal area supports the holder 9 of the samples 8 via a support element 72, a slide stone 38 and a mounting part 39. The samples 8 are formed by small plates, similar to how they are depicted in FIG. 3. The holder 9 can be plugged into the mounting part 39 or interchangeably mounted. The mounting part 39 is connected to the slide stone 38, which is mounted in a movable manner with little friction in the x-y direction in the support element 72 for centering the holder 9 or the samples 8, e.g. by combination of two linear guides. A lower end of the support element 72 can be connected, for example, screwed or welded, to the flat spring 10, particularly to its middle area. The flat spring 10 rests on two supports 31, 33, which are movably guided towards each other in a groove 75 of the base plate 37. To this end, the supports 31, 33 are mounted by pins 36 in grooves 35 running spirally in a—as clear from FIGS. 5 and 5A—component 34 rotatable in relation to the base plate 37. By twisting the component the position or the distance of the supports 31, 33 can be changed in relation to the middle area of the flat spring 10, whereby the characteristic of the flat spring 10 or its oscillation properties is changed. The twisting of the component 34 can be done manually or automatically with an actuator.

Figure 6:
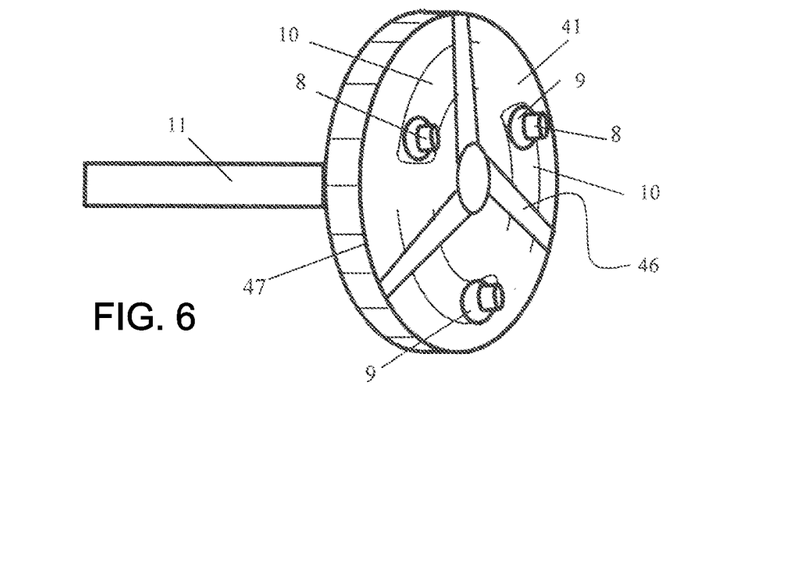
FIG. 6 is a perspective view of a module.
Figure 6A:
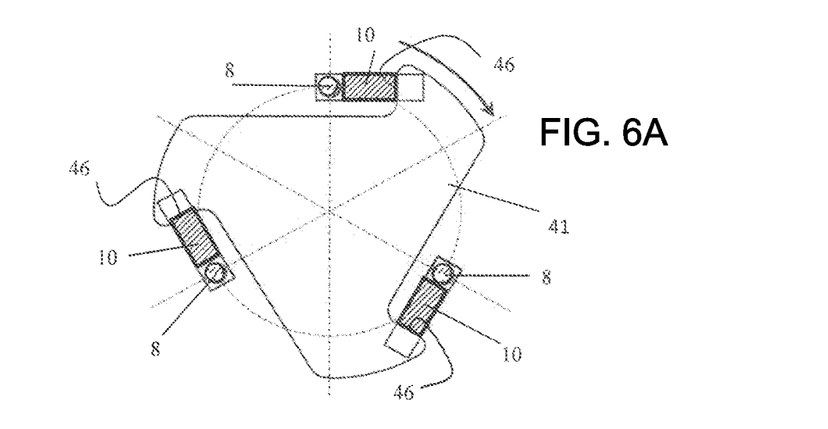
FIG. 6A is an illustration for explaining a principle of the module.
Figure 6B:
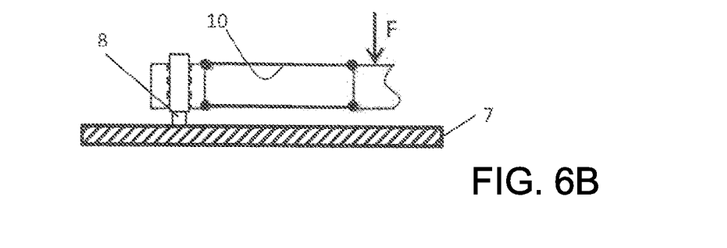
FIG. 6B is an illustration of a part of the module.

FIG. 6 shows another module according to the present invention, which has a carrier 11, which is insertable into the bearing 12 in the base 5 or into a cantilever 33 or into a drive or measurement shaft 6 of the rheometer 1 or can be connected therewith. The carrier 11 supports at least one plate 41 of the type shown in FIG. 6A, to the circumference of which in the plate recesses a number of flat springs 10, in the present case three, extending roughly in the circumferential direction are attached. If necessary, these flat springs 10 could also be integrally configured with the plate 41. In their free end area the respective flat springs 10 bear samples 8, which are configured in the present case as pins. These samples can also readily be formed as balls or have another form. In any case it should be ensured that the arrangement is radially balanced or trued. The individual sectors, which in the present case amount to 120°, of the plate 41 are configured congruent thereto. The samples 8 are pressed with the springs 10 against an opposite sample 7, e.g. a disk or a ring, which is depicted in FIG. 6B. FIG. 6A shows a schematic top view of the plate 41 and FIG. 6B a detailed view through a spring 10 with inserted, pin-shaped sample 8. In addition, an elastomer can also be inserted between the springs as an attenuator, in order to damp the amplitude of the oscillation system and additionally to change the oscillation characteristic.

Figure 6C:
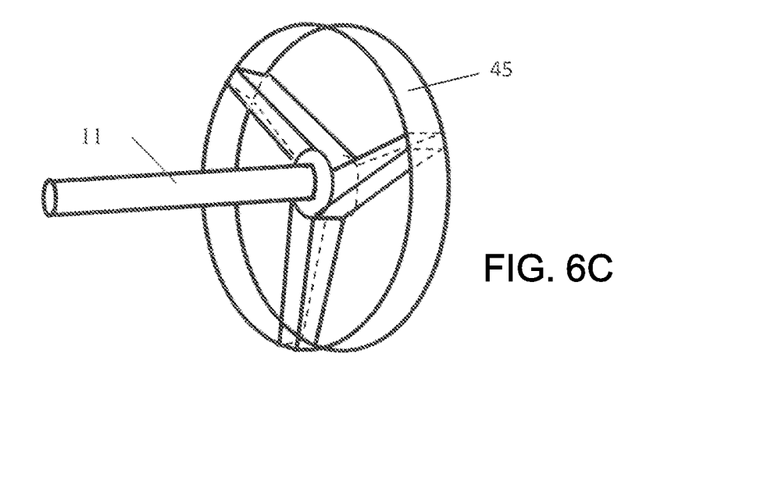
FIG. 6C is a perspective view of the module.

FIG. 6C shows a retaining part 45 for two plates 41 attached to the carrier 11. Both of the plates 41 are inserted parallel to each other into the circumferential grooves of the retaining part 45. Furthermore, the retaining part 45 bears a number of essentially pin-shaped clamping components 46 running radially, corresponding to FIG. 6D, the number of which corresponds in particular to the number of preset flat springs 10, so that each free length of the spring 10 can be used with a clamping component 46 of its own having roughly the form of a spoke. The clamping components 46 are rotatable relative to the springs 10 or to the plates 41 about the axis of the carrier 11. Depending on the length of the section of the flat spring 10, which is set by the respective clamping component 46, the oscillation behavior of the flat springs 10 changes.

In the case of the embodiment of a module or rheometer 1 depicted in FIG. 6 a separate spring system of the individual samples 8 thus occurs. As arises from FIGS. 6 and 7, the plate 41 can be provided twice and both parallel plates 41 can be connected to each other by the holder 9, so that each sample 8 is connected via its holder 9 with two springs 10 or suspended by the latter, which bear the samples 8 via the holder 9. The module is rotated with a drive motor and/or measurement motor during the measurement.

Figure 6D:
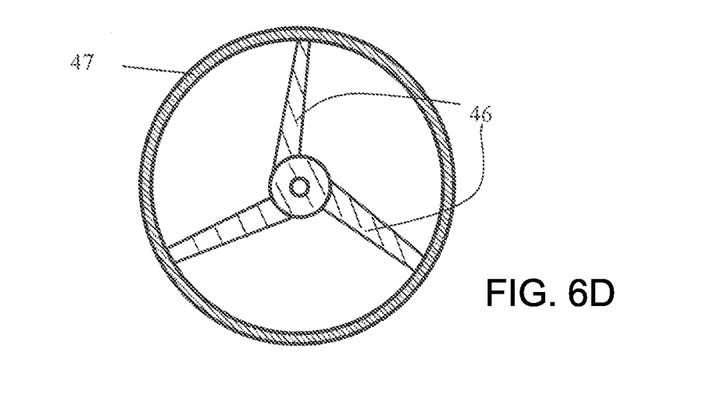
FIG. 6D is an illustration of a part of the a module.
Figure 7:
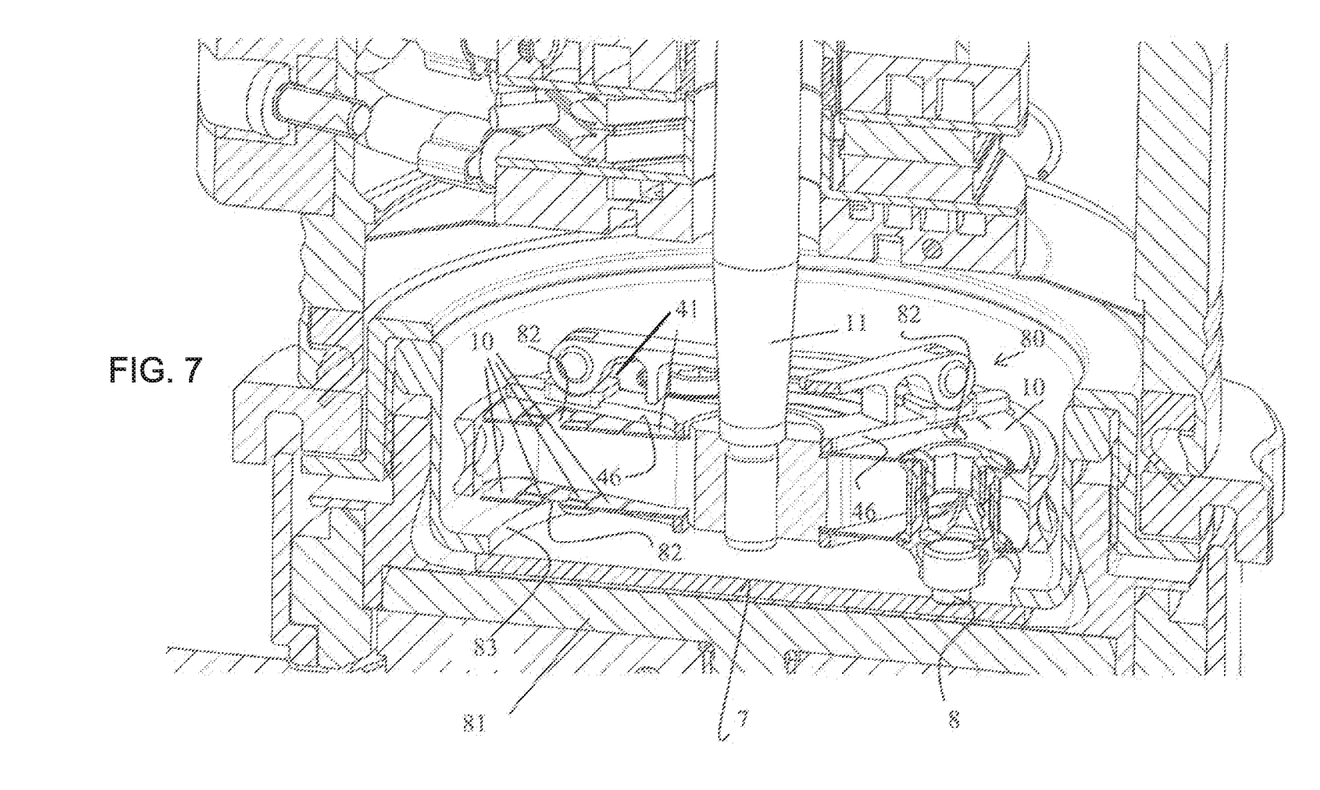
FIG. 7 is a sectional view of a second embodiment of the module similar to the module depicted in FIGS. 6 to 6D in a tribocell.

FIG. 7 shows a module installed in a rheometer 1 according to FIGS. 6 to 6D. This module differs slightly from the module depicted in FIGS. 6 to 6D, namely in respect to the loading of the flat springs 10 by the spokes 46 as well as the form of the plate 41 and the flat springs 10. The flat springs 10 are formed integrally from the plate 41 and show circumferential slots 82 for the feed-through of spring dowel pins and fixing of the spokes 46 in any circumferential position. In this modified embodiment the spokes 46 can be firmly connected with the flat springs 10 in a defined position by a swivel lock 80.

Furthermore, in FIG. 7 the lower sample 7 configured in the form of a plate can be recognized. In this embodiment the carrier 11 depends on the overhanging arm 33 of a rheometer and is rotated. To temper the upper sample 8 tempering units 82 not further eluciated can be provided, which if necessary provide tempering fluid in the chamber with the samples 8. The plate-shaped sample 7 can be fixed and held with a wall 83 forming the space around the sample 8 or around the module.

As arises from FIG. 7, the sample 7, which is configured in the form of a plate can lie motion-invariant on a tempering part 81 and in this embodiment forms the sample 7 positioned below. The sample 8 positioned above in this case is rotated via the carrier 11 relative to the sample 7, wherein the samples 8 are in tribological contact with the sample 7 configured as a disk.

If a rheometer is used with a rotation motor and a measurement motor separate from each other the movement of the module with the upper samples 8 can be limited to a power provision and the lower sample 7 in the form of the plate 41 can be rotated. In particular, if the module is rotated during the measurement, it is advantageous if the entire springy arrangement or the module is configured light and rotationally symmetric to prevent imbalances.

Figure 8:
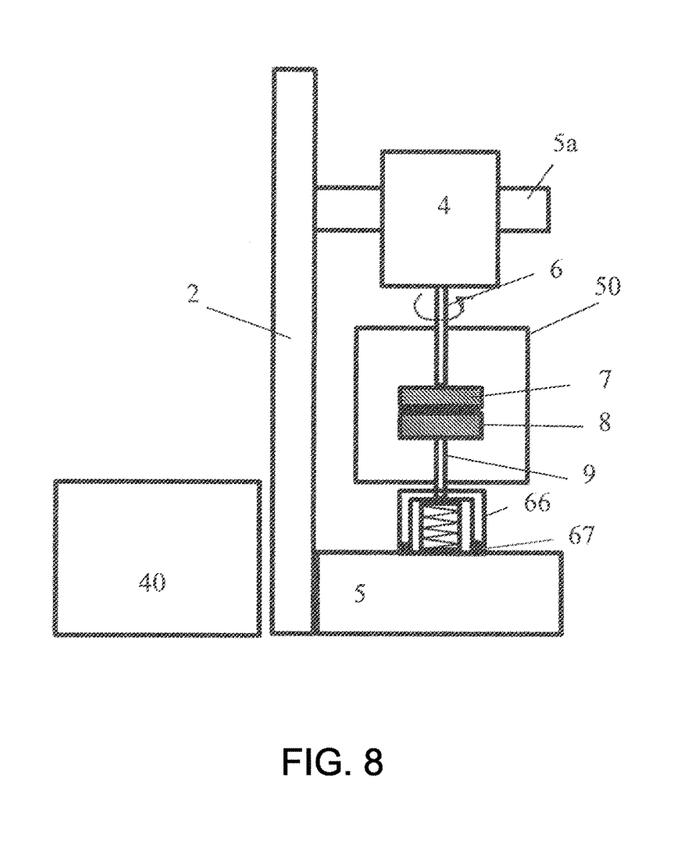
FIGS. 8 to 10 are illustrations showing different possibilites for changing the oscillation properties by changing the mass or by damping.

FIG. 8 shows an embodiment of the rheometer 1 with a spring element, in which the damping of the oscillations is accomplished by a pot or bracket 66 attached to the spring 10 or borne by the latter. The bracket 66 is supported by an elastomer-ring 67, which rests on the base 5 and against which the bracket either lies permanently or can be applied in the area of the lower dead center of the oscillation of the spring 10. Depending on the hardness of the elastomer used the damping of the oscillatory circuit is changed differently. A change of the elastomer rings 67 can, for example, be made after opening or removing the bracket and exchanging the elastomers.

Figure 9:
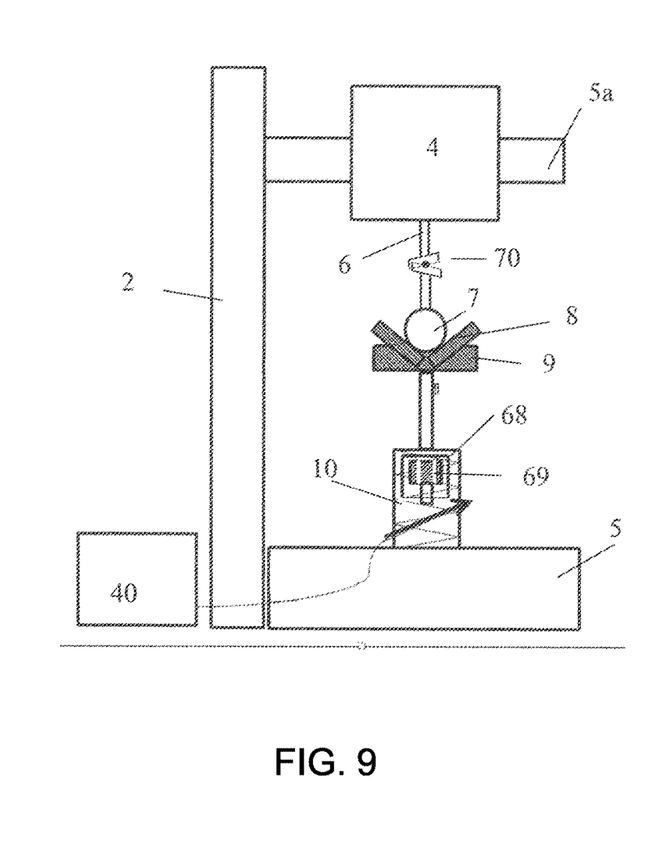

In the case of the embodiment according to FIG. 9 the ball-shaped sample 7 is rotated with the drive shaft 6. The sample 8 in the form of a number of small plates lies on the holder 9. The angles of the plates to the horizontal can thereby be set arbitrarily. In the drive shaft 6 of the sample 7 a cardan joint 70 is formed, in order to center the sample 7 driven by the measurement shaft 6. In principle, other torsionally-stiff hinged shaft connections can also be used instead of the depicted cardan joint, such as cv-joints or ball couplings. Such joints and couplings can also facilitate the required radial-offset and angular offset, however, also cause a decreased or changed compliance of the rheometer.

The attenuator in the case of this embodiment consists of a pot 68 and a piston 69, which is adjustable for height within the pot 68. The pot 68 and the piston 69 are connected to the spring 10 bearing the holder 9, namely at areas of the spring 10 spaced apart from each other. In the case of a movement or oscillation of the spring 10 the piston 69 movable in the pot 68 damps the spring oscillations. The piston 69 can move in a lubricant or oil, which is located within the pot 68. This arrangement could be considered to be a significantly simplified form of a hydraulic damper, which is connected to the ends of the spring 10. The damping characteristic can be influenced via the reduction of the fluid flow, for example, by a throttle valve in the damper.

Figure 10:
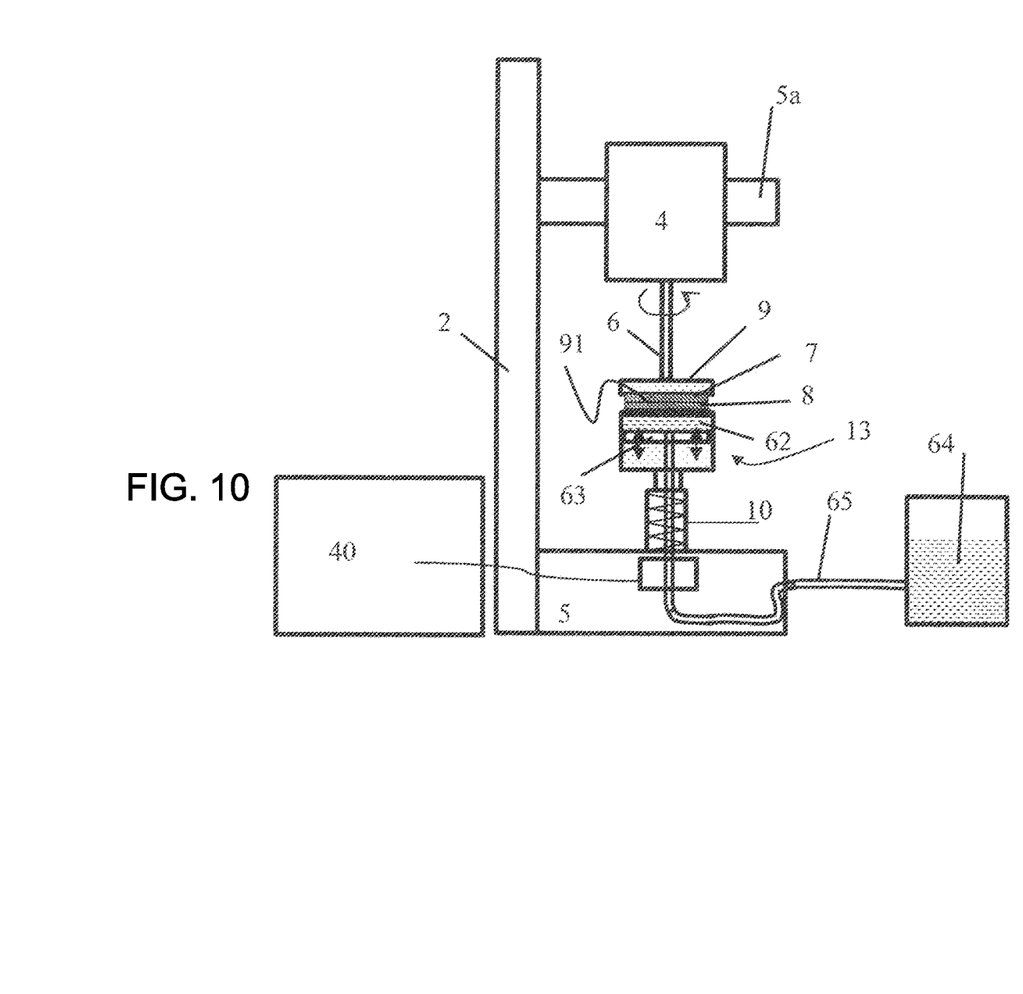

FIG. 10 shows an arrangement, in which a tribology cell or module is inserted into the rheometer 1, which has two plate-shaped samples 7, 8 pressed against each other, wherein between the samples contact material 91 is inserted, which co-determines the frictional contact between the sample areas 7, 8. At the same time, the sample 8 is supported by a holder configured as container 62, in which a piston 63 is movable up and down. Depending on the direction of movement of the piston, fluid can thereby flow from a reservoir 64 into the container 62 or flow out of it and the container dimensions adjust to the volume of the fluid. The holder 9 as well as the piston 63 and the container 62 are supported by the spring 10. The automatic adjustment of the oscillation characteristic is therefore made via the filling of the container 62 or the change of mass associated with it.

A highly flexible hose 65 leading to the container 62 changes the oscillation behavior of the spring unit 3, which contains the spring 10 and the holder 9, only slightly and connects the reservoir 64 with the container. The type of application of pressure and filling can be carried out automatically both through movement of the piston as well as through the application of pressure on the reservoir 64 via the evaluation and control unit 40 and is not shown in detail here.

Another alternative would be the use of expanding vessels, such as membranes, balloons, and the like, which can be filled in a manner analogous to container 62 and adjust their volume to the amount of fluid.

The change of the mass of the spring unit 3 can, for example, also occur through magnetically attachable particles. As a rule, relatively small parts are involved, which can be readily inserted into the modules according to the present invention.

The components can also, for example, be inflatable containers, which depending on their inner pressure can be applied more or less strongly to the holder 9 of the samples 7, 8 and thus damp those of the spring unit 3.

The invention claimed is:

1. An apparatus selected from a group consisting of modules for a rheometer and tribology cells for the rheometer, the apparatus comprising:
    a holder for holding at least one sample under test;
    at least one spring having a holding area for supporting said holder or the one sample;
    a carrier for inserting into a drive of the rheometer or a mounting part of the rheometer or said carrier can be connected to the rheometer, said carrier bearing said at least one spring;
    said spring and said holder or said holding area are regarded as parts of a mechanical oscillation system having oscillation properties;
    an adjustment unit configured to adjust the oscillation properties of said mechanical oscillation system;
    a clamping component; and
    at least one plate supported by said carrier and from said plate said at least one spring departs in a form of a flat spring aligned parallel to said plate, said plate in a free end area and said holder supports the sample, wherein said clamping component provided for said flat spring, with said clamping component a body of said spring is loadable and securable in respect to a plate distance from different, continuously changeable installation positions, wherein said clamping component having a form of spokes rotatable about said holder, which can be applied against said flat spring aligned in a circumferential direction of said plate and can be fixed in different installation positions.

2. The apparatus according to claim 1, wherein said spring is one of a plurality of springs.

3. The apparatus according to claim 1, wherein the sample is held with said holder on said spring in said holding area of said spring or is directly fastened to said spring.

4. The apparatus according to claim 3, wherein the sample is screwed in, clamped, or welded on said spring.

5. An apparatus selected from a group consisting of modules for a rheometer and tribology cells for the rheometer, the apparatus comprising:
    a holder for holding at least one sample under test;
    at least one spring having a holding area for supporting said holder or the sample;
    a carrier for inserting into a drive of the rheometer or a mounting part of the rheometer or said carrier can be connected to the rheometer, said carrier bearing said at least one spring;
    said spring and said holder or said holding area are regarded as parts of a mechanical oscillation system having oscillation properties;
        an adjustment unit configured to adjust the oscillation properties of said mechanical oscillation system, said adjustment unit having friction parts supported on said spring;
    via said adjustment unit, a spring constant of said spring is alterable and said adjustment unit having at least one component applicable against or applying a load to said spring, which adjusts a spring-effective length of said spring; and/or
    via said adjustment unit a mass borne by said spring is alterable and said adjustment unit having a container disposed on said spring and/or on said holder for a defined input or removal of a medium being a liquid; and/or
    said adjustment unit having an element mechanically damping a movement of said spring and/or of said holder and/or of said sample through frictional resistance.

6. An apparatus selected from a group consisting of modules for a rheometer and tribology cells for the rheometer, the apparatus comprising:
    a holder for holding at least one sample under test;
    at least one spring having a holding area for supporting said holder or the sample;

a carrier for inserting into a drive of the rheometer or a mounting part of the rheometer or said carrier can be connected to the rheometer, said carrier bearing said at least one spring;

said spring and said holder or said holding area are regarded as parts of a mechanical oscillation system having oscillation properties;

an adjustment unit configured to adjust the oscillation properties of said mechanical oscillation system;

supports;

said spring is a flat spring disposed horizontally and supported on said supports lying on both sides of a longitudinal middle area of said flat spring;

a slide stone guided movably in an x-y direction;

said holder for the sample is supported in said longitudinal middle area of said flat spring via said slide stone;

a base plate having spiral grooves formed therein; and said supports are adjustable along said flat spring, at a same time and with a same feed, wherefore, said supports are guided into said spiral grooves of said base plate disposed beneath said flat spring and are disposed movably towards each other or away from each other during a twisting of said spiral grooves in a longitudinal direction of said flat spring.

* * * * *